(12) United States Patent
Kim

(10) Patent No.: US 7,045,000 B2
(45) Date of Patent: May 16, 2006

(54) AIR CLEANER WITH AROMA GENERATION

(76) Inventor: Kil Ho Kim, #806-305 Midi Apt., 60-4, Banpo Dong, Seocho-Ku, Seoul (KR)

( * ) Notice: Subject to any disclaimer, the term of this patent is extended or adjusted under 35 U.S.C. 154(b) by 366 days.

(21) Appl. No.: 10/723,876

(22) Filed: Nov. 26, 2003

(65) Prior Publication Data

US 2005/0066818 A1     Mar. 31, 2005

(30) Foreign Application Priority Data

Sep. 29, 2003    (KR) .................. 10-2003-0067411

(51) Int. Cl.
 *B01D 50/00* (2006.01)
(52) U.S. Cl. .................. 96/222; 261/30; 261/DIG. 88; 422/124; 239/59
(58) Field of Classification Search .............. 96/222; 261/30, DIG. 88; 422/124; 239/58, 59
See application file for complete search history.

(56) References Cited

U.S. PATENT DOCUMENTS 5,735,918 A * 4/1998 Barradas ...................... 96/222

6,877,674 B1 * 4/2005 Choquet ...................... 239/58

FOREIGN PATENT DOCUMENTS

JP        2003-161482        6/2003

* cited by examiner

*Primary Examiner*—Robert A. Hopkins
(74) *Attorney, Agent, or Firm*—Brooks Kushman P.C.

(57) ABSTRACT

An air cleaner with aroma generation is disclosed. The air cleaner comprises a main body 10 formed with an outlet 11 for discharging the air filtered by the air filter; a fan installed inside of the main body 10 and forcing the filtered air to be discharged through the outlet 11; a receiving case 20 installed into the main body 10 and having first through-slits 21 formed on circumferential surface and hooking holes 22 in the shape of arc formed at an end thereof; a rotating case 30 for receiving an aroma pack, the rotating case being inserted into the receiving case 20 and having second through slits 31 corresponding to the first slits 21 formed along circumferential surface and hooks 32 formed at an end thereof for being hooked on the hooking holes 22, wherein the first through-slits 21 may or may not overlap with the second through-slit 31 depending on rotation angle of the rotating case 30 about an axis 33 while the hooks 32 are hooked on the hooking holes 22; and a lid 40 for opening and closing the rotating case 30.

3 Claims, 6 Drawing Sheets

AIR CLEANER WITH AROMA GENERATION

BACKGROUND OF THE INVENTION

1. Field of the Invention

The present invention relates to an air cleaner, and more particularly to an air cleaner for generating aroma.

2. Description of the Related Art

People in these modern days spend most of their time inside of building and air in the building accommodating many people is liable to get polluted. There are many reports saying that the air pollution inside of the building is much more severe than the outside of the building. In particular, the air pollution inside of the building becomes severe as an enclosed-type building without a window is constructed. The air is not get polluted only by foreign substances floating in the air, such as dusts and furs, but also by many kinds of a bad smell and an offensive odor. If the air remains in an enclosed space without ventilation, the air pollution gets more and more serious and does harm to human body. Thus, the air cleaner should remove the bad smell and the odor as well as the foreign substances in the air.

SUMMARY OF THE INVENTION

The present invention provides an air cleaner capable of solving the above-described problems. Thus, an object of the present invention is to provide an air cleaner, which effectively removes odors in the air and generates aroma being good for human health.

Another object of the present invention is to provide an air cleaner capable of generating the aroma by circulation of the air.

According to an aspect of the present invention, there is provided an air cleaner with aroma generation comprises:

an air filter;

a main body 10 formed with an outlet 11 for discharging the air filtered by the air filter and a fan installed inside of the main body 10 and forcing the filtered air to be discharged through the outlet 11;

a receiving case 20 installed into the main body 10 and having first through-slits 21 formed on circumferential surface and hooking holes 22 in the shape of arc formed at an end thereof;

a rotating case 30 for receiving an aroma pack, the rotating case being inserted into the receiving case 20 and having second through slits 31 corresponding to the first slits 21 formed along circumferential surface and hooks 32 formed at an end thereof for being hooked on the hooking holes 22, wherein the first through-slits 21 may or may not overlap with the second through-slit 31 depending on rotation angle of the rotating case 30 about an axis 33 while the hooks 32 are hooked on the hooking holes 22; and a lid 40 for opening and closing the rotating case 30.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
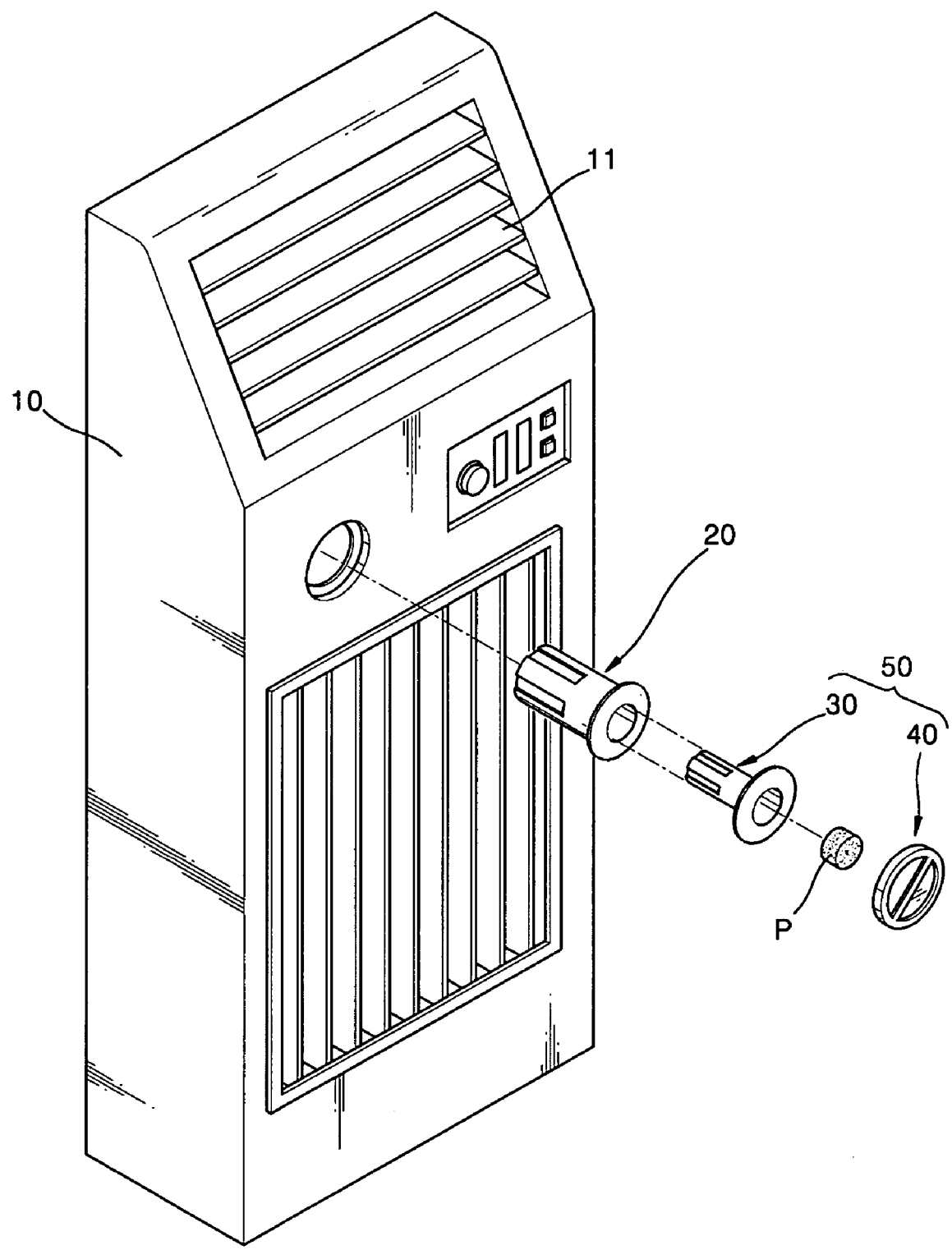
FIG. 1 is a perspective view of an air cleaner with aroma generation according to the present invention.

Referring to FIG. 1, an air cleaner of the present invention includes a air filter (not shown) for filtering air, a main body 10 formed with an outlet 11 for discharging the filtered air and a fan (not shown) installed in the main body 10 and forcing the filtered air to be circulated and discharged through the outlet 11. Here, a receiving case 20 is located adjacent to the outlet 11 and an aroma generation unit 50 is inserted into the receiving case 20.

Figure 2:
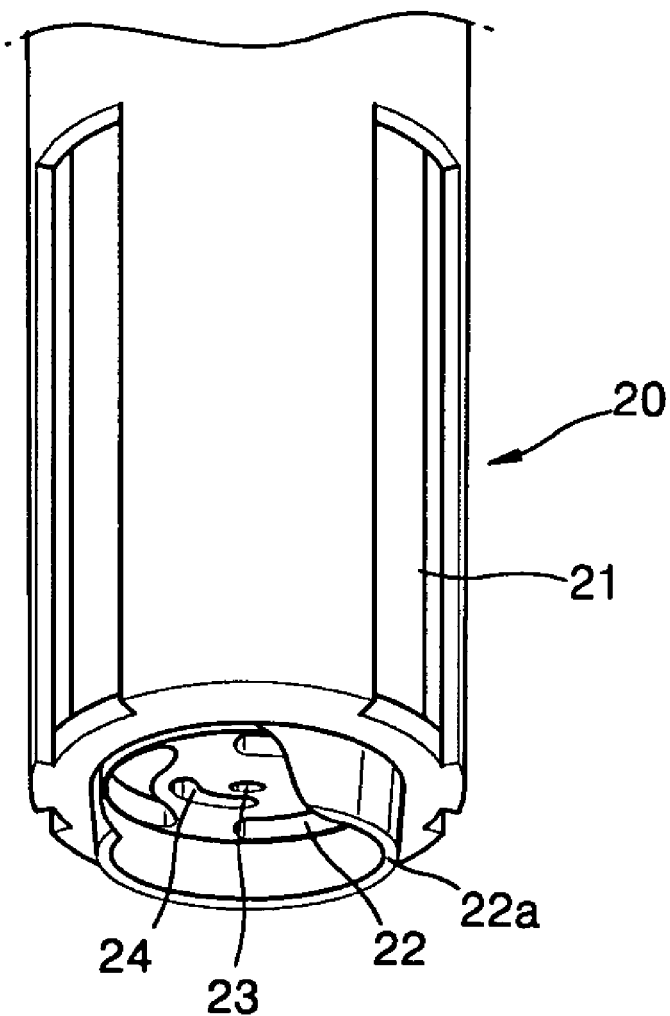
FIG. 2 is a partial-extracted view of a receiving case shown in FIG. 1.
Figure 4:
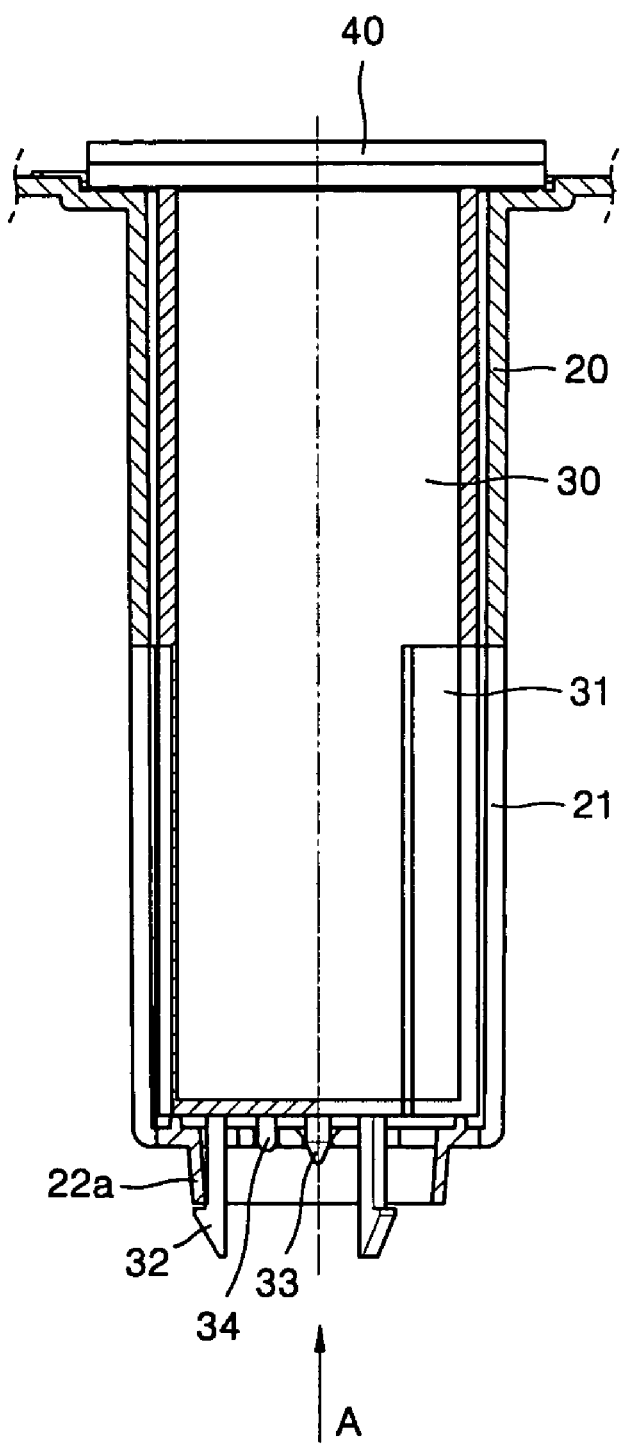
FIG. 4 is an explanatory view of the receiving case coupled with the rotating case and the cover shown in FIG. 1.
Figure 5:
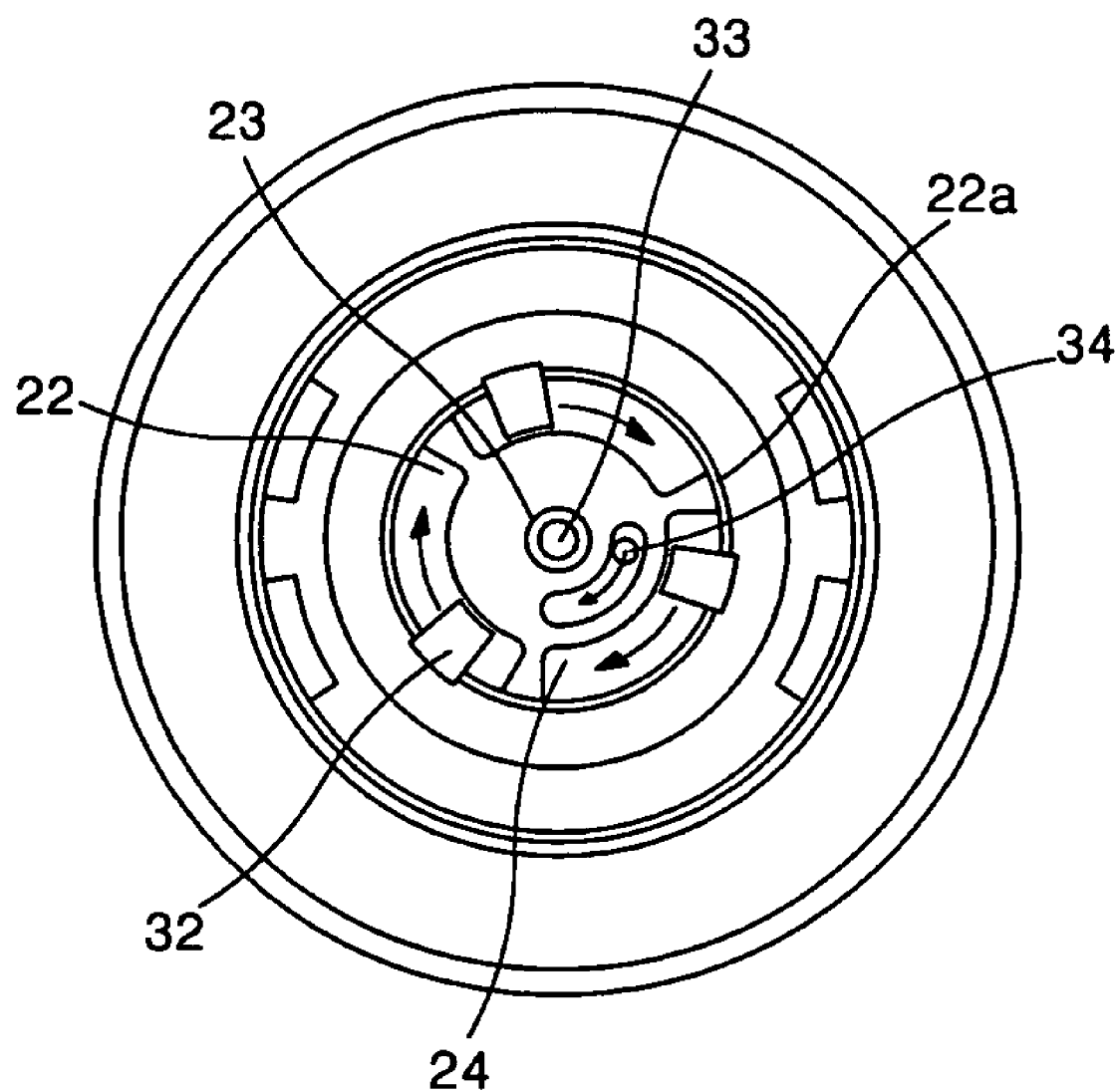
FIG. 5 is a bottom view of FIG. 4, which is shown in a direction designated with an arrow A.

As shown in FIG. 2, the receiving case 20 is installed in the main body 10. The receiving case 20 has first through-slits formed on circumferential surface of the receiving case 20. In the embodiment shown in FIG. 2, there is provided with 4 pieces of first through-slits 21. Also, there is a plurality of hooking holes 22 in the shape of arc formed at an end of the receiving case 20. In the embodiment shown in FIG. 2, three pieces of hooking holes 22 is formed at an end of the receiving case 20 at an interval of 120°. Further, a center hole 23 is formed at a center of the end of the receiving case 20 and a restricting hole 24 is formed between the hooking holes 22 and the center hole 23. Here, as shown in FIG. 2, it is preferable to form a hooking rim 22a projecting downward along an edge of the hooking holes 22. As will be described in detail with reference to FIG. 4, hooks 32 are inserted through the hooking holes 22 to be hooked onto the hooking rim 22a.

Figure 3:
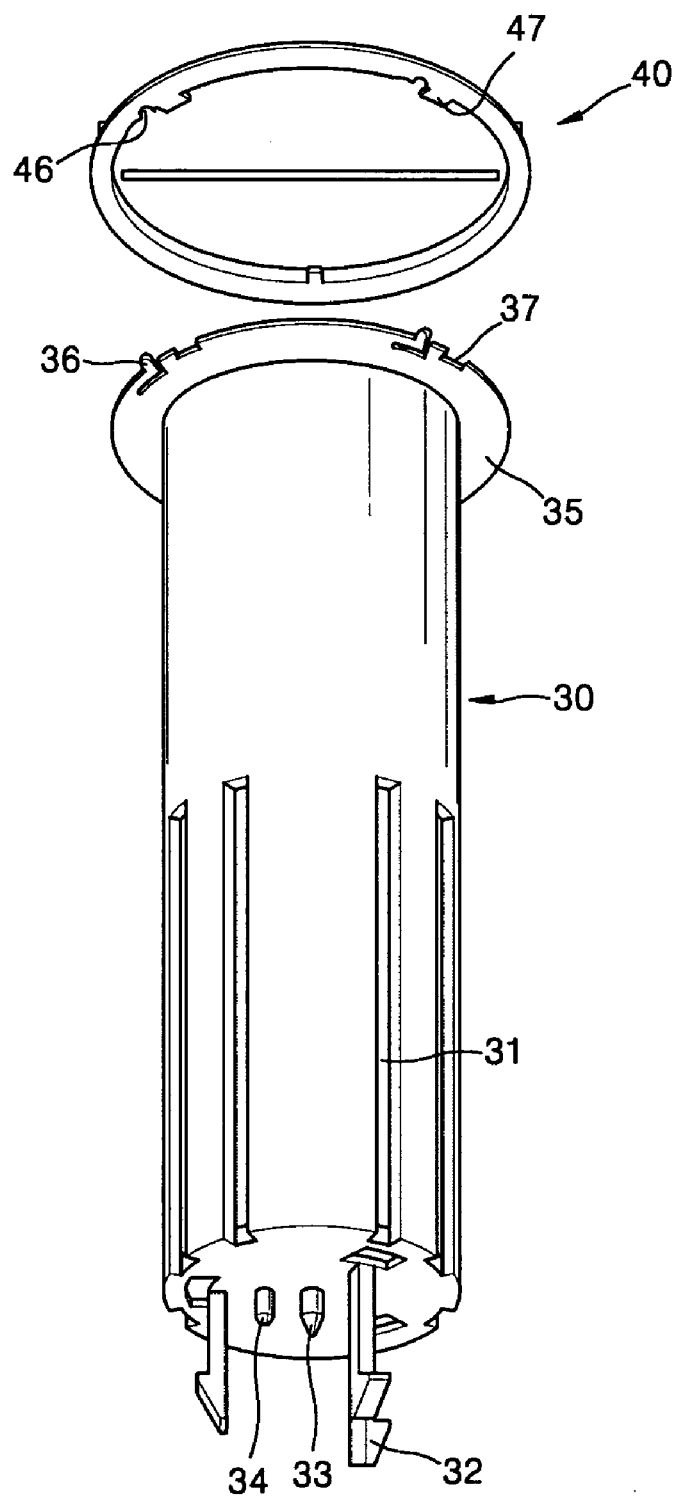
FIG. 3 is a partial-extracted view of a rotating case and a cover shown in FIG. 1.

Referring to FIG. 3, the aroma generation unit 50 comprises a rotating case 30, which receives an aroma pack P therein and may be rotated with a predetermined angel, and a lid 40 capable of opening and closing the rotating case 30.

Second through-slits 31 corresponding to the first through slits 21 are formed on the circumferential surface of the rotating case 30. In the embodiment shown in FIG. 3, there is provided with 6 pieces of the second through-slits 31. There is formed with 3 pieces of the hooks 32 at an end of the rotating case 30. The hooks 32 are inserted through the hooking holes 22. After the insertion through the hooking holes 22, the hooks 32 are hooked onto the hooking rims 22a formed along the edge of the hooking holes 22.

An axis 33 is formed at an end of the rotating case 30 and the axis 33 is to be inserted into the center hole 23. Also, a restricting protrusion 34 is formed between the hooks 32 and the axis 33 and the restricting protrusion 34 is to be inserted into the restricting hole 24.

A flange 35 is formed at the other end of the rotating case 30. Along an edge of the flange, there are provided with protrusions 36 elastically projecting in a radial direction and flange grooves 37 formed with partially cut-away portion.

Figure 6:
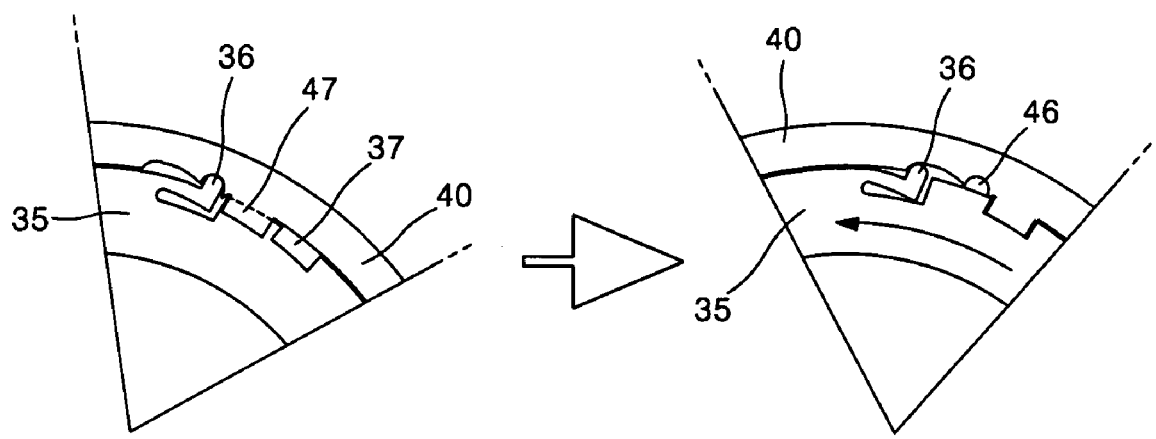
FIG. 6 is an explanatory view showing a flange and the cover in a coupled state.

The lid 40 may be engage/disengage with the flange 35. On an inner circumference of the lid 40, there are provided with hooking grooves 46 hooked by the protrusion 36, and hooking protrusions 47. The hooking protrusions 47 can pass through the flange grooves 37 to be hooked onto a lower surface of the flange 37. With the construction as shown in FIG. 6, the hooking protrusions 47 should be located at the flange grooves 36 while an user closes and opens the lid 40.

In a state that the hooks 32 are inserted through the hooking holes 22, the rotating case 30 can be rotated about the axis 33 with a predetermined angle. Due to the rotation of the rotating case 30 relative to the receiving case 20, the first through-slits 21 may or may not overlap with the second through-slits 31. In other words, when the first through slits 21 overlaps with the second through-slits 31, the aroma generated from the aroma pack P is ready to be discharged into the main body 10 of the air cleaner. On the contrary, when the first through-slits 21 does not overlap with the second through-slit 31, the aroma can not be discharged into the main body 10 of the air cleaner.

In an operation of the fan (not shown), the air coming from outside of the air cleaner passes through the filter (not shown) to be discharged through the outlet 11. Here, depending on the rotational position of the rotating case 30 with the aroma pack P, it is possible to change discharging quantity of the aroma. The aroma dispersed in the main body 10 will be mixed with the filtered air and discharged outside of the air cleaner through the outlet 11. The aroma does not only remove odour in the air, but also make the air aromatic. Thus, it is possible to make the environment comfortable and perform an aromatic therapy.

As described herein above, the aroma may be used so as to attain the pacification, the sterilization and the insect-proof. Also, the aroma can be used for relaxing mind, stimulating brain and controlling emotion as well as purifying the air. Further, many kinds of the aromas may be selected depending on the purpose of its use.

The air cleaner of the present invention has such a construction in that fragrant component and deodorant component of the aroma are mixed with the inflow air in front of the outlet of the air cleaner. Thus, the fragrant component and the deodorant component of the aroma may effectively reduce the odour component involved in the filtered air without affecting purification of the air in the air cleaner.

Further, an amount of the aroma discharged into the main body 10 can be increased or decreased by rotating the rotation case 30 to change the overlapping area between the first through-slits 21 and the second through-slits 31.

As described, the air cleaner with aroma generation according to the present invention cannot only reduce the odour in the purified air, but also make the environment comfortable by generating the aroma.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An air cleaner with aroma generation, the air cleaner comprising
    a main body 10 formed with an outlet 11 for discharging air filtered by an air filter
    a fan installed inside of the main body 10 and forcing the filtered air to be discharged through the outlet 11;
    a receiving case 20 installed into the main body 10 and having first through-slits 21 formed on circumferential surface and hooking holes 22 in the shape of arc formed at an end thereof;
    a rotating case 30 for receiving an aroma pack, the rotating case being inserted into the receiving case 20 and having second through slits 31 corresponding to the first slits 21 formed along circumferential surface and hooks 32 formed at an end thereof for being hooked on the hooking holes 22, wherein the first through-slits 21 may or may not overlap with the second through-slit 31 depending on rotation angle of the rotating case 30 about an axis 33 while the hooks 32 are hooked on the hooking holes 22; and
    a lid 40 for opening and closing the rotating case 30.

2. An air cleaner as claimed in claim 1,
    wherein a center hole 23 is formed at a center of the end of receiving case 20 and a restricting hole 24 is formed between the hooking holes 22 and the center hole 23;
    wherein an axis 33 is formed at an end of the rotating case 30 and the axis 33 is to be inserted into the center hole 23; and,
    wherein a restricting protrusion 34 is formed between the hooks 32 and the axis 33 and the restricting protrusion 34 is to be inserted into the restricting hole 24.

3. An air cleaner as claimed in claim 1.
    wherein a flange 35 is formed at the other end of the rotating case 30 and the flange 35 has along it edge protrusions 36 elastically projecting in a radial direction and flange grooves 37 formed with partially cut-away portion; and,
    wherein hooking grooves 46 hooked by the protrusion 36, and hooking protrusions 47 passing through the flange grooves 37 to be hooked onto a lower surface of the flange 37 is formed on an inner circumference of the lid 40.

* * * * *